United States Patent [19]

Rehder

[11] 4,284,080
[45] Aug. 18, 1981

[54] APPARATUS FOR THE WORKING OF A BONE WHICH IS TO BE PROVIDED WITH A SHELL PROSTHESIS

[75] Inventor: Günther Rehder, Stuhr, Fed. Rep. of Germany

[73] Assignee: Orthoplant Orthopädische Implantate GmbH & Co. KG, Bremen, Fed. Rep. of Germany

[21] Appl. No.: 42,870

[22] Filed: May 29, 1979

[30] Foreign Application Priority Data

Aug. 4, 1978 [DE] Fed. Rep. of Germany ....... 2834297

[51] Int. Cl.³ ..................... A61F 17/32; A61B 17/16; A61B 17/14; A61F 5/04
[52] U.S. Cl. .................................... 128/305; 128/310; 128/317; 128/92 CA; 128/92 E; 128/92 EB
[58] Field of Search ...................... 128/321, 305, 305.1, 128/304, 310, 312, 317, 92 E, 92 B, 92 C, 92 CA, 92 EB, 300; 30/276

[56] References Cited

U.S. PATENT DOCUMENTS

| 847,133 | 3/1907 | Velasco | 128/305.1 |
| 3,667,456 | 6/1972 | Charnley | 128/305 |
| 4,004,581 | 1/1977 | Heimke et al. | 128/92 E |
| 4,059,115 | 11/1977 | Jumashev et al. | 128/310 |
| 4,069,824 | 1/1978 | Weinstock | 128/317 |
| 4,116,200 | 9/1978 | Braun et al. | 128/305 |

FOREIGN PATENT DOCUMENTS

| 2543723 | 4/1977 | Fed. Rep. of Germany | 128/305 |
| 2284308 | 4/1976 | France | 128/92 E |

Primary Examiner—Robert W. Michell
Assistant Examiner—C. W. Shedd
Attorney, Agent, or Firm—Toren, McGeady and Stanger

[57] ABSTRACT

Apparatus for the working of a bone, especially the femur head of a human hip joint, wherein the bone is to be provided with a shell-shaped endoprosthesis, is disclosed. The apparatus includes a drivable drive shaft having a free end and a pot-shaped cutting head being arranged on the free end of the drive shaft. The cutting head is open outwardly and has a guiding bore forming part of the cutting head and is centrally located thereon. The guiding bore extends in an axial direction of the drive shaft. The cutting head has an inner end face and a jacket portion on which cutting elements are arranged. Finally included is a guiding pin for cooperating with the guiding bore. The guiding pin is arranged centrally in the bone section to be treated and protrudes from the bone surface. Additional central cutting means arranged on the cutting head are disclosed.

11 Claims, 2 Drawing Figures

APPARATUS FOR THE WORKING OF A BONE WHICH IS TO BE PROVIDED WITH A SHELL PROSTHESIS

FIELD OF THE INVENTION

The invention relates to an apparatus for the working of a bone, especially the femur head of a human hip joint, which bone is to be provided with a shell-shaped endoprosthesis.

BACKGROUND OF THE INVENTION

For different diseases and injuries of a hip joint, so-called total endoprostheses are known which consist of two parts. One part is a shell, consisting of a plastic material which is generally compatible with tissue, wherein the shell is cemented in the hip pan after previous cutting. The other part is a prosthesis portion, being longitudinal and relatively large, and consisting generally of a suitable steel alloy. At the end of the prosthesis portion there is arranged a sphere which substitutes for the femur head of the injured bone. The sphere passes over a transition part and over a flange into a curved shaft, which is inserted in the bone, after previous separation of the top of the femur neck, and is anchored in the bone with bone cement.

With these known total endoprostheses, positive results have been achieved, in comparison with the previously known possibilities for treatment of such fractures and diseases, like arthroses and the like. However, the complication rate is unsatisfactory due to the relatively radical operation of the body which is to be treated. During such an operation, a considerable amount of bone has to be removed which, under circumstances such as wear phenomena of the hip joint, is not injured but is unusable for the planned bearing function. This results in the use of other treating methods in the case of wear phenomena such as arthroses and the like.

Therefore, these radical operations are avoided, if they are not, because of certain fractures, absolutely necessary. Especially in the case of wear phenomena of joints, attempts have been made to substitute for the sliding areas which are especially important for the function of the respective joint and are, simultaneously, subject to great loads, without removing its supporting substructure. This has been accomplished, for example, by cementing a shell-shaped pan of suitable plastic material or ceramic in a hip joint pan similar to the previously described total endoprosthesis. Furthermore, the counter-sliding surface for the artificial hip joint pan has also been substituted for by a shell, consisting of metal, namely, of a suitable steel. This surface is shaped on its outer side as a spherical segment, whose vertical height is generally somewhat smaller than its transverse dimension, i.e., smaller than the radius of curvature of the outer side of the segment.

To attach such a metal shell on the femur head, the end face of the femur head has to be adapted to the curve of the metal shell. Moreover, the femur head has to be treated in extension of its end face, i.e., on its jackets, in order to adapt the femur head to the corresponding dimensions of such a shell prosthesis.

It turns out now that these necessary treatments of a bone which is to be provided with a shell prosthesis, are relatively time-consuming and, therefore, extend the operation time.

Furthermore, there is the particular disadvantage that there cannot be produced precise fitting areas when cutting the sphere-shaped and the cylindrical end sections of the respective bone portions, because the freely guided instrumentation is not able to fulfill this requirement. Moreover, during the treatment of the bone, the instrumentation often removes tissue material at a point where, due to the existing strength, there is an especially small treatment resistance. At such points, however, there is no need to remove any or, at least, not so much tissue material. Such a free treatment of a bone leads, however, not only to imprecise fitting areas but, there is also basically no possibility to arrange the implant physiologically in axis alignment, which is particularly desirable especially in highly stressed joints.

Furthermore, free treatment of a bone is also of disadvantage, when several operation steps are performed one after another because, during a subsequent treatment step, possibly satisfactory intermediate results can be diminished with regard to other fitting areas or the like.

OBJECTS OF THE INVENTION

Therefore, an object of the present invention is to create an apparatus of the type described, with which precise fitting areas can be produced during the treating of the bone, so that a physiologically axis-aligned arrangement of the implant can be guaranteed. This is to be done without removing tissue material which should remain per se. Furthermore, the invention encompasses the possibility, depending on the design of the implant, to use, if necessary, further treatment steps, without any deterioration of the previously achieved results. Simultaneously, the apparatus according to the invention should achieve a considerable reduction of the treatment time, in addition to the better results.

SUMMARY OF THE PRESENT INVENTION

These objects are achieved by the apparatus according to the invention, which is characterized by a drivable drive shaft, on whose free end there is arranged a pot-shaped cutting head which is open outwardly and has a centered guiding bore for a guiding pin wherein the guiding bore extends in the axial direction of the drive shaft. The guiding pin is essentially arranged in the bone central to the bone section to be treated, and protrudes essentially perpendicular from the bone surface. There are also arranged cutting means on the inner end face and on the jacket of the cutting head.

For a better understanding of the present invention, reference is made to the following description and accompanying drawings, while the scope of the present invention will be pointed out in the appended claims.

DESCRIPTION OF THE PREFERRED EMBODIMENTS

Figure 1:
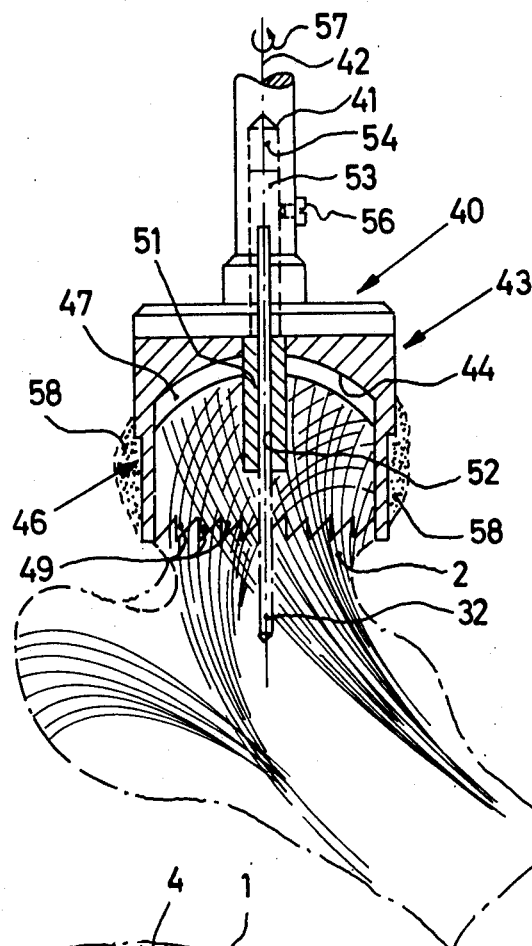
FIG. 1 shows a side view of the apparatus according to the invention, partially in section, wherein the apparatus is applied to the femur head of a hip joint bone after the cutting process has just been finished.

Referring initially to FIG. 1, shown there in solid lines is an apparatus 40 for treatment of a bone which is to be provided with a shell-shaped endoprosthesis, which bone is the femur head 2 of a human hip joint.

The apparatus 40 has a drive shaft 41 which is drivable by a drive, not shown, and is to be rotated about its longitudinal axis 42. On the lower free end of the drive shaft 41, there is located a pot-shaped cutting head 43 which is open outwardly, and is provided on its inner end face 44 and on its jacket 46 with cutting means.

The cutting means 47, arranged on the end face 44 of the cutting end 43, have a circular, arc-shaped curvature which corresponds to the curve of the shell-shaped endoprosthesis which is to be applied. Thus, in the present case, this curvature corresponds to the curve of the second femur head shell 6 (FIG. 2), which will be explained below.

The cutting means 47 consists of six replaceable knives which are arranged with respect to each other by the same dividing angle. In FIG. 1, there are shown only two such opposite knives.

The cutting means 48, arranged on the jacket 46 of the cutting head 43, includes cutting teeth 49 which are constructed on the end face of the free edge of the cutting head 43. The teeth 49 are uniformly spaced along the periphery.

Further, the cutting head 43 includes a third cutting means 51 which centrally extends from its end face 44 to its open end, and is constructed as a shank cutter. The third cutting means 51 includes a guiding bore 52, extending in its axial direction and, therefore, in the direction of the axis 42 of the drive shaft 41. The diameter of the guiding bore 52 is considerably smaller than the diameter of the shank cutter 51, as can be seen from FIG. 1. The diameter of the shank cutter 51 is optimally 8 mm.

The third cutting means 51, formed as a shank cutter, is replaceable. It includes a peg section 53 which extends into the drive shaft 41, and fits in a bore 54 of the drive shaft 41, where it is made fixed with a screw 56. Since the bore 54 has the appropriate length, it is possible to adjust the axial extension of the shank cutter 51.

Before starting the actual treatment of the femur head 2, a guiding pin 32 is shot into the femur head 2. This guiding pin is a so-called Kirschner wire.

The guiding pin 32, then, protrudes centrally relative to the femur head which is to be treated, and perpendicularly from the bone surface of the femur head 2, so that the treatment apparatus 40 can be centered on it.

For this purpose, the apparatus 40 is shifted with its guiding bore 52 on the guiding pin 32 until a contact occurs between the apparatus 40 and the femur head 2 which is to be treated.

Then, the apparatus 40 is moved in rotation through the drive shaft 41, in the direction of the arrow 57. The cutting teeth 49 start to remove the tissue, shown by the stippling in FIG. 1, to create a cylindrical jacket on the femur head 2.

Shortly afterwards (if necessary, simultaneously or shortly before), the third cutting means 51, formed as a shank cutter or as a twist drill, starts to cut a blind hole into the femur head 2.

Thereby, the apparatus 40 is lowered downwardly by means of the guiding bore 52 along the guiding pin in axis alignment until, finally, the knives 47 of the cutting means disposed on the end face 44 of the cutting head 43, also engage with the femur head 2 and, therefore, can produce a spherical area on its end face.

FIG. 1 of the drawing shows the end condition of the treatment.

The apparatus 40 is then removed from the femur head 2. According to the development or design of the shell prosthesis, the construction of the prosthesis can be started.

Figure 2:
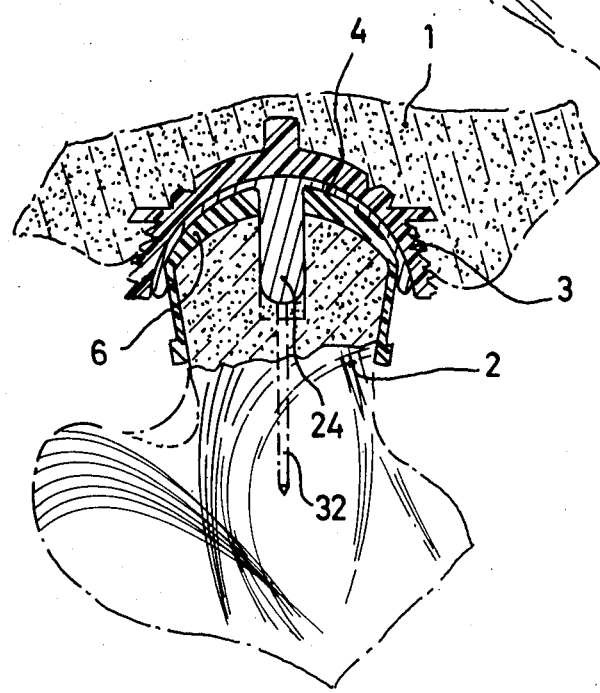
FIG. 2 illustrates, in a similar side, partial sectional view, the hip joint, partially shown in FIG. 1, after insertion of the shell prosthesis.

In a particular development of the prosthesis, shown in FIG. 2, the cylindrically cut jacket of the femur head 2 is, in addition, previously conically cut by a suitable knife head wherein the bore in the femur head 2 created by the third cutting means 51, can serve as a centering bore for such a knife head. In this manner, the precise fitting areas previously created are not damaged during further treatment.

After the acetabulum has also been treated in a suitable manner and has been provided with an acetabulum pan 3 (FIG. 2), the femur head shell is then inserted.

The femur shell in the embodiment of FIG. 2 is of two-piece design, and consists of an inner shell 6 of plastic material, as well as of an outer femur head shell 4 of metal which includes a guiding peg 24. The guiding peg 24 protrudes through a bore in the inner femur head shell 6 and extends into the bore created by the third cutting means 51. Accordingly, this bore in this embodiment serves not only for centering during the treatment but also for centering of the femur head shell. Therefore, the guiding pin ensures a precise alignment of the fitting areas.

It is obvious that with the apparatus according to the invention, it is not only possible to perform a very fast treatment of the bone which is to be treated but also enables the treatment to be extremely precise. This is done by virtue of the guiding or centering, respectively, so that exact fitting areas are created. Since the existing centering arrangement can be used also by the actual prosthesis shell, the desired physiological axis-aligned arrangement of the implant is guaranteed.

As described above, the cutting means, arranged on the inner end face of the cutting head, include preferably a curve which corresponds to the curve of the inner surface of the shell-shaped endoprosthesis, the inner surface facing towards the bone, wherein the curve is preferably in the shape of a circular arc. The cutting means consist, in a preferable development of the present invention, of at least four, preferably six, exchangeable knives, which are preferably angularly offset. The knives have, preferably, essentially the same dividing angle.

As further described previously, the cutting means, which are arranged on the jacket of the cutting head, can be fixed on the edge of the pot-shaped cutting head, preferably on its end face, and can be constructed as cutting teeth uniformly spaced along the edge of the pot-shaped cutting head.

It is also preferred that the cutting head be provided with a third cutting means centrally extending from its end face to its open end, wherein this third cutting means is constructed in the form of a shank cutter or of a twist drill, and can include the guiding bore for the guiding pin.

The third cutting means is preferably replaceable and can extend with one section into the drive shaft and can be attached there with a suitable fastening element like, for example, a screw. When the third cutting means extends beyond the edge of the cutter, there is achieved an especially good observation possibility, during the application of the third cutting means on the guiding pin.

Since, on the other hand, it is required that only as little tissue material be removed as possible, the third cutting means should have a length so that it will terminate within the pot-shaped cutter. According to a preferred embodiment, the axial extension of the third cutting means is adjustable so that both advantages can be achieved if necessary.

While the foregoing description and drawings represent the preferred embodiments of the present invention, it will be obvious to those skilled in the art that various changes and modifications may be made therein without departing from the true spirit and scope of the present invention.

LIST OF REFERENCE NUMERALS

1 Acetabulum
2 Femur head
3 Acetabulum pan
4 Outer shell of the femur head
6 Inner shell of the femur head
24 Guiding peg
32 Guiding pin (Kirschner wire)
40 Treatment apparatus
41 Drive shaft
42 Longitudinal axis
43 Cutting head
44 (inner) End face (of 43)
46 Jacket
47 Cutting means (on 44)
48 Cutting means (of 46)
49 Cutting teeth
51 (third) Cutting means
52 Guiding bore (in 51)
53 Peg section (of 51)
54 Boring (in 41)
56 Screw
57 Arrow
58 Tissue

What is claimed is:

1. Apparatus for the working of a bone, especially the femur head of a human hip joint, which bone is to be provided with a shell-shaped endoprosthesis, comprising:
a drivable drive shaft having a free end;
a pot-shaped cutting head arranged on the free end of said drive shaft, said cutting head has an inner end face which faces away from said drive shaft free end and surrounds the axis of said drive shaft, and a circular free edge on said cutting head which edge is concentric with the axis of said drive shaft;
first cutting means arranged at the inner end face of said cutting head for defining an arcuately shaped surface on the bone which surface corresponds to the inner surface of the shell-shaped endoprosthesis which is to be applied to the bone;
second cutting means including uniformly spaced cutting teeth arranged at said free edge of said cutting head for defining a cylindrical jacket on the bone;
third cutting means extending from said inner end face of said cutting head away from said drive shaft for providing a cylindrical bore in the bone concentric with the axis of said drive shaft, said third cutting means having a central guiding bore extending in the axial direction of said drive shaft; and
a guiding pin for cooperating with said guiding bore to guide said cutting head through the bone, said guiding pin to be arranged in a bone section treated such that said pin protrudes from the bone and is alignable with said guide bore.

2. Apparatus according to claim 1, wherein said first cutting means includes a plurality of knives which are angularly offset relative to one another.

3. Apparatus according to claim 2, wherein adjacent ones of said knives are offset from each other by substantially equal angles.

4. Apparatus according to claim 2, including at least four knives.

5. Apparatus according to claim 2, including six knives.

6. Apparatus according to claim 2, wherein said knives are arranged to be interchangeble.

7. Apparatus according to claim 1, wherein said third cutting means is arranged to provide a cylindrical bore of a diameter in the range of from about 4 to 10 mm.

8. Apparatus according to claim 7, wherein said third cutting means is arranged to provide a cylindrical bore of a diameter of about 8 mm.

9. Apparatus according to claim 1, wherein said third cutting means is arranged to be exchangeable.

10. Apparatus according to claim 9, wherein said third cutting means includes a protruding portion arranged to extend into said drive shaft, and including a fastening element for attaching said protruding portion onto said drive shaft.

11. Apparatus according to claim 1, including means for adjusting the axial length of said third cutting means.

* * * * *